(12) United States Patent
Hubbard, Jr. et al.

(10) Patent No.: US 7,336,187 B2
(45) Date of Patent: Feb. 26, 2008

(54) PATIENT ACTIVITY MONITOR

(75) Inventors: James E. Hubbard, Jr., Derry, NH (US); Micahel D. Healy, Boston, MA (US); Marianne Mastrangelo, Lynnfield, MA (US)

(73) Assignee: The Trustees of Boston University, Boston, MA (US)

(*) Notice: Subject to any disclaimer, the term of this patent is extended or adjusted under 35 U.S.C. 154(b) by 356 days.

(21) Appl. No.: 10/531,486

(22) PCT Filed: Oct. 20, 2003

(86) PCT No.: PCT/US03/33248

§ 371 (c)(1),
(2), (4) Date: Apr. 15, 2005

(87) PCT Pub. No.: WO2004/036390

PCT Pub. Date: Apr. 29, 2004

(65) Prior Publication Data

US 2005/0242946 A1    Nov. 3, 2005

Related U.S. Application Data

(60) Provisional application No. 60/419,640, filed on Oct. 18, 2002.

(51) Int. Cl.
*G08B 23/00* (2006.01)

(52) U.S. Cl. .............. 340/573.1; 340/506; 340/517; 340/521; 340/524; 340/525; 340/539.11; 340/539.12; 340/286.07; 340/825.19

(58) Field of Classification Search ............ 340/573.1, 340/506, 517, 521, 524, 525, 539.1, 539.11, 340/539.12, 286.02, 286.07, 825.19
See application file for complete search history.

(56) References Cited

U.S. PATENT DOCUMENTS

| | | | |
|---|---|---|---|
| 4,216,462 A | 8/1980 | McGrath et al. ............. 340/150 |
| 4,237,344 A * | 12/1980 | Moore ......................... 379/38 |
| 5,319,363 A * | 6/1994 | Welch et al. ........... 340/825.36 |
| 5,537,459 A * | 7/1996 | Price et al. .............. 455/435.1 |
| 5,549,113 A | 8/1996 | Halleck et al. .............. 128/671 |
| 5,576,952 A * | 11/1996 | Stutman et al. ............. 600/300 |
| 5,689,229 A * | 11/1997 | Chaco et al. .......... 340/286.07 |
| 6,093,146 A | 7/2000 | Filangeri .................... 600/300 |
| 6,125,350 A * | 9/2000 | Dirbas .......................... 705/2 |
| 6,665,385 B2 | 12/2003 | Rogers et al. .............. 379/106 |
| 6,876,303 B2 * | 4/2005 | Reeder et al. ........... 340/573.1 |
| 6,958,706 B2 * | 10/2005 | Chaco et al. .......... 340/870.11 |
| 7,092,376 B2 * | 8/2006 | Schuman .................... 370/349 |
| 7,138,902 B2 * | 11/2006 | Menard ..................... 340/5.53 |

\* cited by examiner

*Primary Examiner*—Daryl C Pope
(74) *Attorney, Agent, or Firm*—Weingarten, Schurgin, Gagnebin & Lebovici LLP

(57) ABSTRACT

A patient activity monitoring system that allows caregivers of multiple patients to work more efficiently and with reduced cost, while increasing the quality and level of patient care. The system includes a plurality of remote monitoring subsystems, a plurality of user notification units, and a central monitoring unit with a Graphical User Interface (GUI) communicably coupled between the remote monitoring and user notification units. Each remote monitoring subsystem includes a remote monitoring unit, and a sensor device associated with a respective patient that detects one or more activity and/or physiological parameters of the patient. A simplified user interface including the GUI and the user notification units provides indications of the type and level of assistance required by one or more patients to caregivers at centralized and remote locations.

32 Claims, 9 Drawing Sheets

| Work Flow | Sys. Cnfg. | Legend | BMS/Pager/Nrs |

•••• | 228 | <<Patient Name>> | Activity Log>> | Spec Instruc.>> primary: #1     secondary: #1     Last check: AM; (0 min.)     Alarms History
<nurse name>   <nurse name>                                    0 | 0 | 0 | 0
backup page in: 4:00 min

| Work Flow | Sys. Cnfg. | Legend | BMS/Pager/Nrs |

12:49:02AM; Aug 22 | Activity Log:
Shift 1 | Shift 2 | Shift 3
S. Mary, CRN | #8

266-WC:GREEN, Patient Norminal 12:47:49
266-WC: YELLOW, Patient Check 12:47:49
266-WC:GREEN, Alarm Reset 12:47:49 AM    — 814

| Jess K., CNA | #1 | (228) (222) (224) (226) 228 ○ ○ ○ ○ ○ |
| Beth L., CNA | #2 | (251) (252) (261) (254) (255) (256) (257) (258) (259) (260) |
| Ragina M., CNA | #3 | (221) (223) 225 (227) (229) 231 (233) 235 237 (239) |
| R-J Smith., CNA | #4 | 238 230 232 234 236 ○ ○ ○ ○ ○ |
| Mary-Ann N., CNA | #5 | 260 261 262 263 264 (265) (266) ○ ○ ○ |
| Jane D., CNA | #6 | ○ ○ ○ ○ ○ ○ ○ ○ ○ ○ |
| Betty S., CNA | #7 | ○ ○ ○ ○ ○ ○ ○ ○ ○ ○ |

802    806    804

| Work Flow | Sys. Cnfg. | Legend | BMS/Pager/Nrs |

| 12:51:38 AM; Aug 22 | Activity Log: |
|---|---|
| Shift 1 | Shift 2 | Shift 3 | 266-WC:GREEN, Patient Norminal 12:47:49 |
| | 266-WC: YELLOW, Patient Check 12:47:49 |
| S. Mary, CRN #8 | 266-WC:GREEN, Alarm Reset 12:47:49 AM |

Shift 1:
 Jess K., CNR

Display Name: #1 Waveware
serial no.: 2092001
frequency: 457.5875 MHz
cap code: 0001001

Shift 2: <nurse name>
Shift 3: <nurse name>

Betty S., CNA #7

| Work Flow | Sys. Cnfg. | Legend | BMS/Pager/Nrs |

| 12:51:38 AM; Aug 22 | |
|---|---|
| Shift 1 | Shift 2 Shift 3 | 263-WC:BLUE, System Ready 12:47:49 |
| | 263-WC:GREEN, Patient Norminal 12:4 |
| S. Mary, CRN #8 | 263-B :GREEN, B Configuration 12:47:4 |
| | 264-WC:BLUE, System Ready 12:47:49 |
| Jess K., CNA #1 | 264-WC:GREEN, Patient Norminal 12:4 |
| | 264-B :GREEN, B Configuration 12:47:4 |
| Beth L., CNA #2 | 265-WC:BLUE, System Ready 12:47:49 |
| Ragina M., CNA #3 | 265-WC:GREEN, Patient Norminal 12:4 |
| | 265-WC:RED!, Incontinance 12:47:49A |
| R-J Smith., CNA #4 | 265-WC:GREEN, Alarm Reset 12:47:49 |
| Mary-Ann N., CNA #5 | 266-WC:BLUE, System Ready 12:47:49 |
| | 266-WC:GREEN, Patient Norminal 12:4 |
| Jane D., CNA #6 | 266-WC:YELLOW, Patient Check 12:47 |
| Betty S., CNA #7 | 266-WC:GREEN, Alarm Reset 12:47:49 |

FIG. 9b 906

PATIENT ACTIVITY MONITOR

CROSS REFERENCE TO RELATED APPLICATIONS

This application claims priority of U.S. Provisional Patent Application No. 60/419,640 filed Oct. 18, 2002 entitled PATIENT ACTIVITY MONITOR.

STATEMENT REGARDING FEDERALLY SPONSORED RESEARCH OR DEVELOPMENT

N/A

BACKGROUND OF THE INVENTION

The present application relates generally to patient monitoring systems, and more specifically to a patient activity monitoring system providing a simplified user interface, customizable alarms, and automatic customized report generation. The presently disclosed patient activity monitoring system enables caregivers to work more efficiently and with reduced cost, while increasing the quality and level of care provided to patients.

Patient monitoring systems are known that employ advanced sensor, electronics, and communications technologies for remotely monitoring one or more characteristics of a patient. For example, a conventional patient monitoring system may comprise a remote monitoring unit associated with a patient, a central monitoring unit, and a communications device for establishing a communications link between the remote monitoring unit and the central monitoring unit. The remote monitoring unit typically employs a sensor for generating data representative of, e.g., a measured physiological characteristic of the patient such as the patient's heartbeat. Further, the communications device typically establishes a communications link for transmitting the patient data from the remote unit to the central unit either periodically or when a predetermined warning limit is exceeded. Upon receipt of the patient data, the central monitoring unit may then provide a visible and/or audible indication to a caregiver at the centralized location indicating whether or not the patient requires immediate attention.

Although patient monitoring systems like the conventional system described above have generally enhanced the quality of care given to patients, such patient monitoring systems have drawbacks when employed in settings such as hospital wards and nursing homes. In such settings, the patients requiring intermittent or continuous monitoring may significantly outnumber the caregivers available at the hospital or nursing home location. Further, each patient may have more than one condition that needs to be monitored. Still another drawback of conventional systems is that they often generate false alarms because they typically do not adequately monitor large sensing areas, i.e., conventional systems typically fail to provide large aperture sensing. As a result, patients may wander off the sensed area, thereby causing false alarms to be generated. Possible solutions to these problems include increasing the number of patient monitoring systems and/or the number of caregivers at the hospital or nursing home site. However, both of these solutions can significantly increase the cost of providing quality health care to patients.

Not only may certain physiological characteristics such as the heartbeat of a patient require monitoring by caregivers, but certain activities of patients may also require significant caregiver supervision. For example, there may be problems associated with a patient getting out of bed without supervision or assistance. Such a patient may suffer a fall resulting in substantial physical injury. In the event a patient requires extended bed rest to recover from a fall, he or she may require assistance to turn over after being inactive in bed for an extended period of time. Moreover, such a patient may experience incontinence or may simply become agitated from the extended bed rest. In each case, the patient may require assistance from a caregiver whose attention may currently be directed toward another patient at the healthcare facility. Conventional patient monitoring systems like the system described above generally do not provide caregivers the information they need to operate efficiently and with a high degree of care in settings such as hospital wards and nursing homes, in which each caregiver may be responsible for multiple patients requiring various types and levels of assistance.

It would therefore be desirable to have a patient monitoring system that allows caregivers of multiple patients to operate more efficiently and with reduced cost. Such a system would allow data to be collected over time so that data mining can be used to observe trends in caregiver response, fall trends, etc. Caregivers may then use this data to generate intervention plans for specific patients in order to improve the quality and level of care, as required.

BRIEF SUMMARY OF THE INVENTION

In accordance with the present invention, a patient activity monitoring system is provided that allows caregivers of multiple patients to work more efficiently and with reduced cost, while increasing the quality and level of patient care. Benefits of the presently disclosed patient activity monitoring system are achieved via a simplified user interface that provides caregivers with visible and/or audible indications of patient status based on the type and level of assistance required by the patient, and that further provides for automatic report generation.

In one embodiment, the patient activity monitoring system comprises a plurality of remote monitoring subsystems, a plurality of user notification units, and a central monitoring unit including a Graphical User Interface (GUI) communicably coupled between the remote monitoring subsystems and the user notification units. In the preferred embodiment, the central monitoring unit is coupled to the remote monitoring subsystems and the user notification units by at least one wireless network. Each remote monitoring subsystem includes a remote monitoring unit and at least one sensor device. Each sensor device is associated with a respective patient. Further, each sensor device is configured to detect one or more predetermined activity and/or physiological parameters of the respective patient, and to transmit data representative of the detected parameter(s) to the remote monitoring unit communicably coupled thereto. Each remote monitoring unit is configured to receive the sensor data, and to transmit patient information corresponding to the sensor data to the central monitoring unit. The patient information is then provided to users of the patent activity monitoring system (e.g., "caregivers") via a simplified user interface implemented by the central monitoring unit and the plurality of user notification units.

In the presently disclosed embodiment, the simplified user interface comprises the GUI of the central monitoring unit, and the plurality of user notification units. For example, each user notification unit may comprise an alphanumeric pager. The GUI is operative to generate a plurality of interactive display screens to allow caregivers to set up and administer the overall patient monitoring system, to access cumulative patient data, to access, generate, and print customized reports, and to receive indications of the current status of one or more patients at a centralized location. Each pager unit similarly provides indications of the current status of one or more patients to caregivers distant from the centralized location. In the preferred embodiment, the indications of the current patient status provided by the GUI and pager units comprise visible and/or audible alarms that can be customized to indicate both the type and level of assistance required by the patient. For example, each alarm may be customized to indicate whether a patient's status is currently unchanged and therefore no assistance is required, or whether the patient is currently out-of-bed, agitated, or incontinent and therefore requires immediate attention.

By providing a patient activity monitoring system with a simplified user interface including customizable a for indicating both the type and level of assistance required by patients, caregivers responsible for multiple patients in hospital ward or nursing home settings can operate more efficiently while enhancing the quality of care provided to their patients.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which:

FIGS. 7a-7c are sample display screens generated by the GUI of FIG. 1 illustrating setup screens for adding/editing patient information;

FIG. 8 is a sample display screen illustrating the overall look-and-feel of the GUI of FIG. 1, including the real-time dynamic workload of selected caregiver shifts;

FIGS. 9a-9b are sample display screens generated by the GUI of FIG. 1 illustrating informational screens indicating the nursing staff and remote monitors associated with a particular pager.

DETAILED DESCRIPTION OF THE INVENTION

U.S. Provisional Patent Application No. 60/419,640 filed Oct. 18, 2002 entitled PATIENT ACTIVITY MONITOR is incorporated herein by reference.

A patient activity monitoring system is disclosed including a simplified user interface that provides users of the system (e.g., "caregivers") with visible and/or audible indications of patient status based in the type and level of assistance required by the patient. The presently disclosed patient activity monitoring system allows caregivers of multiple patients to work more efficiently while increasing the quality and level of patient care.

Figure 1:
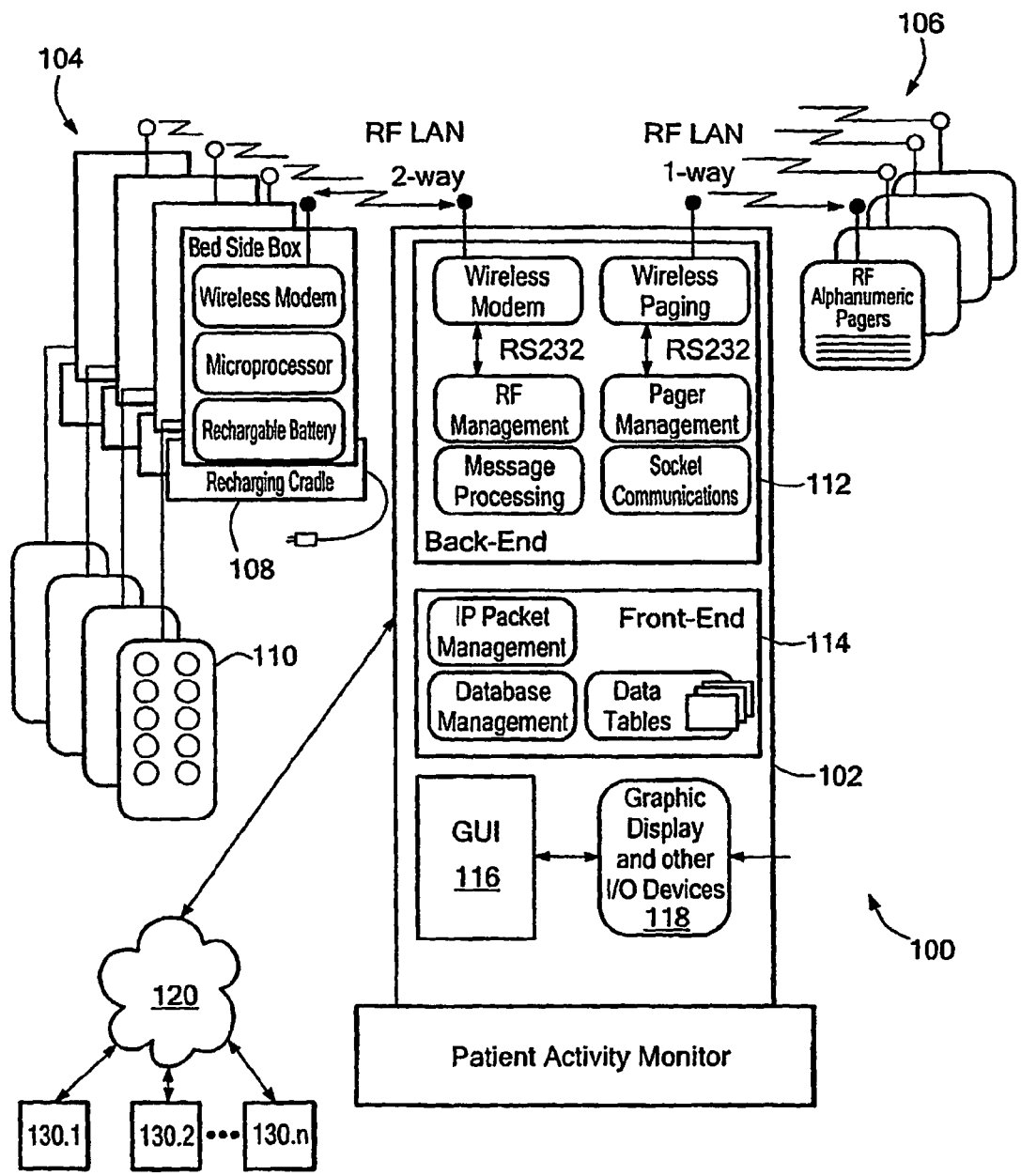
FIG. 1 is a functional block diagram of a patient activity monitoring system comprising remote monitoring subsystems, a central monitoring unit including a Graphical User Interface (GUI), and user notification units according to the present invention.

FIG. 1 depicts an illustrative embodiment of a Patient Activity Monitoring (PAM) system 100, in accordance with the present invention. In the illustrated embodiment, the PAM system 100 comprises a central monitoring unit 102, a plurality of remote monitoring subsystems 104, and a plurality of user notification units 106. The central monitoring unit 102 is communicably coupled to the plurality of remote monitoring subsystems 104 and the plurality of user notification units 106 via respective wireless Local Area Networks (LANs) such as Radio Frequency (RF) LANs or any other suitable wireless network. It is noted that the remote monitoring subsystems 104 and the user notification units 106 may alternatively be coupled to the central monitoring unit 102 by any suitable land-based network. It will be appreciated, however, that the flexibility of the PAM system 100 is enhanced when wireless LANs are employed.

As shown in FIG. 1, each one of the remote monitoring subsystems 104 includes a remote monitoring unit 108 coupled to a sensor device 110. In the preferred embodiment, each sensor device 110 comprises a replaceable laminar sensor pad ("smart sheet"), as disclosed in U.S. patent application Ser. No. 09/791,114 filed Feb. 22, 2001 entitled PATIENT MONITORING SYSTEM EMPLOYING ARRAY OF FORCE SENSORS ON A BEDSHEET OR SIMILAR SUBSTRATE, which is incorporated herein by reference. For example, such smart sheet sensors 110 may be placed under a patient while lying in a bed or seated on a wheelchair to track and chronicle predetermined patient activities as well as physiological characteristics such as heartbeat and respiration. In the presently disclosed embodiment, each smart sheet sensor 110 is configured as a spatial filter. Specifically, patient activity initiates dynamic pressure data that flows from the patient to the spatial filter of the smart sheet sensor 110, which converts the data into information about the patient's position and relative weight. The smart sheet sensor 110 is further configured to provide the patient information to the remote monitoring unit 108 coupled thereto via a suitable sensor interface (not shown).

Each remote monitoring unit 108 includes a suitable microprocessor or single board computer and at least one temporal filter (not shown). The temporal filter is configured to improve the signal-to-noise ratio of the patient information, and the microprocessor or single board computer is operative to convert the patient information into one or more indications of the patient's status, e.g., the patient may be out-of-bed, agitated, or incontinent. It is noted that the microprocessor or single board computer is further operative to convert information relating to the status of the remote monitoring subsystem into one or more indications of the subsystem's status. In the preferred embodiment, the remote monitoring unit 108 performs all of the required analysis of the patient activity information to generate indications of the patients' status, and reduces the analysis to specific messages defined in terms of predetermined data packet protocols. It is noted that each remote monitoring unit 108 may be employed as a remote data logger of patient activities to create an activity database of real-time patient movements, which may be used to develop algorithms for determining the patients' current status. Each remote monitoring unit 108 further includes a wireless modem for communicating with the central monitoring unit 102 over the RF LAN. In the preferred embodiment, each remote monitoring unit 108 has a rechargeable battery and a rechargeable cradle for the convenience of the user.

The central monitoring unit 102 is configured to transmit request messages to the remote monitoring units 108, and to receive information relating to the patients' status from the remote monitoring units 108, over the RF LAN. The central monitoring unit 102 is further configured to transmit notification messages to the user notification units 106, thereby notifying caregivers of patient activity and other conditions that may need their attention. In the preferred embodiment, each user notification unit 106 comprises an alphanumeric pager. In the preferred embodiment, the architecture of the PAM system 100 designates the central monitoring unit 102 as the "hub" for all of the remote monitoring subsystems 108 and all of the alphanumeric pagers 106.

In the illustrated embodiment, the central monitoring unit 102 is operative to perform a plurality of back-end functions 112 and a plurality of front-end functions 114. Specifically, the back-end functions 112 comprise wireless modem functions for providing 2-way communications with the remote monitoring units 108 over the RF LAN, RF management functions, and a suitable communications interface such as an RS232 interface operatively disposed between the wireless modem and the RF manager. The back-end functions 112 further comprise wireless paging functionality for providing 1-way communications with the alphanumeric pagers 106 over the RF LAN, pager management functions, and a suitable communications interface such as an RS232 interface operatively disposed between the wireless paging and the pager manager. In addition, the back-end functions 112 include message processing functionality for handling the request and notification messages, and socket communications functionality for setting up one or more secure communications channels over high-level protocols such as HTTP. The front-end functions 114 comprise IP packet management functions, and database management functions for managing a plurality of data tables. For example, each data table may comprise information relating to the status of a particular patient.

The central monitoring unit 102, which has both socket communications and IP packet management functionality, is configurable to communicate over a Wide Area Network (WAN) such as the Internet 120. For example, users 130.1-130.n such as primary care physicians/providers may communicate with the central monitoring unit 102 over the Internet 120 to access patient information stored in the data tables. Further, the central monitoring unit 102 may be configured for automatically generating customized reports based on the patient information and/or other information entered into the central unit 102 by users of the PAM system 100, and for transmitting the reports over the Internet 120 to selected ones of the primary care physicians/providers 130.1-130.n.

For example, the FileMaker Pro™ software application sold by FileMaker™, Inc., Santa Clara, Calif., USA, may be employed to generate customized reports that are tailored for specific individuals. Such customized reports may include caregiver staffing reports, PAM system fault reports, patient activity log reports, and any other suitable reports. Further, such reports may be transmitted either periodically or automatically over the Internet 120 to one or more specific individuals having a need to know.

As shown in FIG. 1, the central monitoring unit 102 provides a Graphical User Interface (GUI) 116 for assisting users of the PAM system 100 such as caregivers in, e.g., (1) monitoring the dynamic workload of caregivers on a particular shift in real-time, (2) allocating patient/caregiver assignments and concomitant paging hierarchies, (3) displaying patient status in terms of predetermined well-defined activities, (4) logging and archiving patient activities and staff assignments, (5) generating real-time reports of status alarms, staffing trends, and workloads, (6) interfacing with standard databases for report generation, (7) generating reports locally or exporting data for external report generation, (8) customizing patient status alarms to individual patient needs, and (9) running PAM system diagnostics. The GUI 116 communicates with a graphic display and other I/O devices 118.

For example, the central monitoring unit 102 may comprise a Q-TERM-G70 console employing a RISC 92 MHz MIPS R3000 processor, a speaker, a real-time clock, and an Ethernet-enabled graphics terminal with object-based programming. Further, a QVGA 320×240 pixel touch screen color LCD display may be employed to display the GUI 116, and user input programming may be achieved via a resistive touch screen and soft keys located on or around the display area. The central monitoring unit 102 may further comprise an Ethernet 10Base-T interface that supports TCP/IP protocols. It is expected that, for the most part, users of the GUI 116 will have limited technical expertise, and that the GUI 116 will likely be located in a busy area central to the patients' rooms. Accordingly, the GUI 116 is configured to be simple, uncluttered, and easy-to-use.

Figure 2:
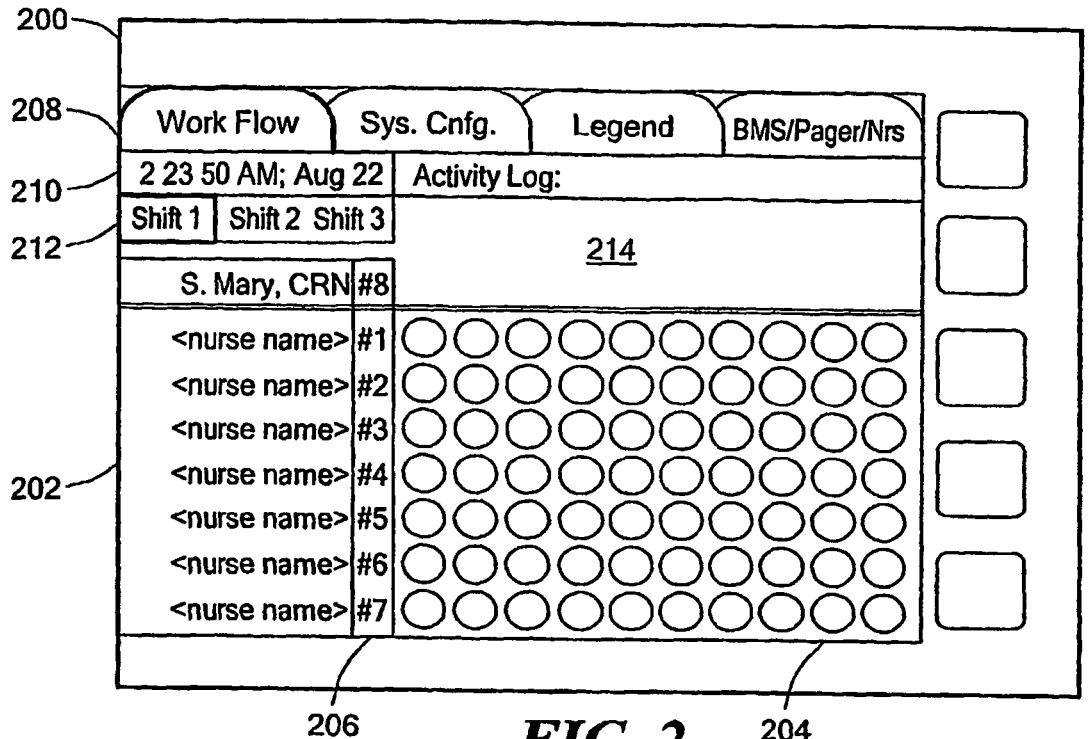
FIG. 2 is a sample display screen generated by the GUI of FIG. 1 illustrating a main display screen of the presently disclosed patient activity monitoring system.

FIG. 2 depicts a sample display screen 200 generated by the GUI 116 of FIG. 1, illustrating the main display screen of the PAM system. In the illustrated embodiment, the main screen 200 is displayed in a work flow mode, which may be employed to show which patient room numbers and pagers are associated with specific caregivers. The caregiver names are indicated in a display area 202, the patient room numbers are indicated in a display area 204, and the pager numbers are indicated in a display area 206.

For example, the main display screen 800 (see FIG. 8) indicates specific associations of caregivers, patient room numbers, and pagers in display areas 802, 804, and 806, respectively. As shown in the illustrative example of FIG. 8, pager #1 and patient room numbers 228, 222, 224, and 226 are associated with caregiver Jess K., Certified Nursing Assistant (CNA); pager #2 and patient room numbers 251-252, 261, and 254-260 are associated with caregiver Beth L., CNA; pager #3 and patient room numbers 221, 223, 225, 227, 229, 231, 233, 235, 237, and 239 are associated with caregiver Ragina M., CNA; pager #4 and patient room numbers 238, 230, 232, 234, and 236 are associated with caregiver R-J Smith, CNA; and, pager #5 and patient room numbers 260-266 are associated with caregiver Mary-Ann N., CNA. As shown in FIG. 8, pagers #6 and #7 are associated with caregivers Jane D., CNA and Betty S., CNA, respectively, however no patient room numbers are currently associated with these caregivers. Further, pager #8 is associated with supervising caregiver S. Mary, Certified Registered Nurse (CRN). It is noted that the color and shape of the patient room identifiers are indicative of the type and level of assistance required by the patient in that room, as further described below.

As shown in FIG. 2, the main screen 200 includes a display area 212 indicating the shift assignment of the caregivers (Shift 1, Shift 2, or Shift 3), a display area 210 indicating the date ("August 22") and time ("2 23 50 AM"), and a plurality of tabs 208 relating to the "Work Flow", System Configuration ("Sys. Cnfg."), "Legend", and Bedside Monitor/Pager/Nurses ("BSM/Pager/Nrs") screens. The main screen 200 further includes a display area 214 indicating an activity log showing the current activity for one or more of the patient rooms (see also display area 814 of FIG. 8).

In the presently disclosed embodiment, the main screen 200 (see FIG. 2) acts as a "home page" for the PAM system 100 (see FIG. 1). Its primary purpose is to provide an at-a-glance summary of all patient statuses. By way of the GUI 116, the main screen 200 conveys the following information: (1) the names of all patients being monitored, (2) the assigned pager, (3) the urgency of patient needs via the color of the patient room identifiers and whether or not the room identifiers are "blinking", and (4) the patient location (e.g., bedside or mobile). It is noted that the blinking of a patient room identifier may also be employed to indicate that an alarm is "in-progress", but has not yet been answered by a caregiver. Once the caregiver responds by pressing a button on the bedside monitor, the blinking stops, the response time is recorded, and the corresponding room identifier turns green.

In the preferred embodiment, the color of the patient room identifiers may be green, yellow, red, or red (blinking). The caregiver can obtain a summary of the meaning of the colors and shapes of the patient room identifiers by pressing the Legend tab displayed on the touch screen, thereby displaying the following information in a pop-up window:

| Status | | |
|---|---|---|
| Bedside | Mobile | ■● URGENT (blinking) |
| ■(green) | ●(green) | No response required. |
| ■(yellow) | ●(yellow) | No immediate response required. |
| ■(red) | ●(red) | Response required. |
| ■(black) | ●(black) | Disabled monitor. |

According to the information listed above, the best case is for all of the icons ■ or ● to be green. The colors yellow and red are employed to indicate two levels of alarm. Because the color red is more visually acute, the more red icons are displayed, the greater the need for immediate patient care to be performed. The blinking red icon is the most visually acute, indicating that a caregiver page is in-progress. The color yellow is used to indicate that the need for patient care is less urgent, i.e., no immediate response required. The color black is used to indicate a disabled monitor.

In the presently disclosed embodiment, preset thresholds (i.e., threshold sensitivities) for the respective alarms may be set by the user via the GUI 116, as further described below. Moreover, in addition to blinking visual alarms on the display screen 200, the user interface of the PAM system provides one or more audible alarms, which may be activated, e.g., when any blinking alarm is allowed to continue beyond a preset time.

In the preferred embodiment, the following associations are recorded via the PAM system:

Pager #⇋Remote monitor⇋Room #⇋Patient name.

The above associations provide the key information needed by caregivers, while minimizing the need to update the associations frequently. In this embodiment, the association of a numbered pager to a numbered remote monitoring unit occurs only once. Further, the pager and remote monitor pair are placed in a given room, and the association of the remote monitor and the room number occurs only once. This association changes when the remote monitor and pager combination is moved to another room. Finally, the patient information is associated with the room number, and this association only changes if the patient were relocated to another room.

As described above, in the event the patient is mobile, this information is reflected by the PAM system in the choice of icon displayed in the Work Flow area of the GUI. Further, a paging hierarchy may be established that allows a primary and a secondary paging protocol. For example, in the event the patient requires immediate assistance, the pager associated with the corresponding remote monitor and room number is alerted first. After a preset time interval, if the primary caregiver assigned to that pager does not respond, a secondary page may be initiated to a back-up caregiver, and so forth. The above-described remote monitoring unit (e.g., Bedside Monitor (BSM)), pager, and caregiver (e.g., Nurse (Nrs)) associations are made using the BSM/Pager/Nrs screen, which the user may access via the GUI by pressing the BSM/Pager/Nrs tab displayed on the touch screen.

Figure 3:
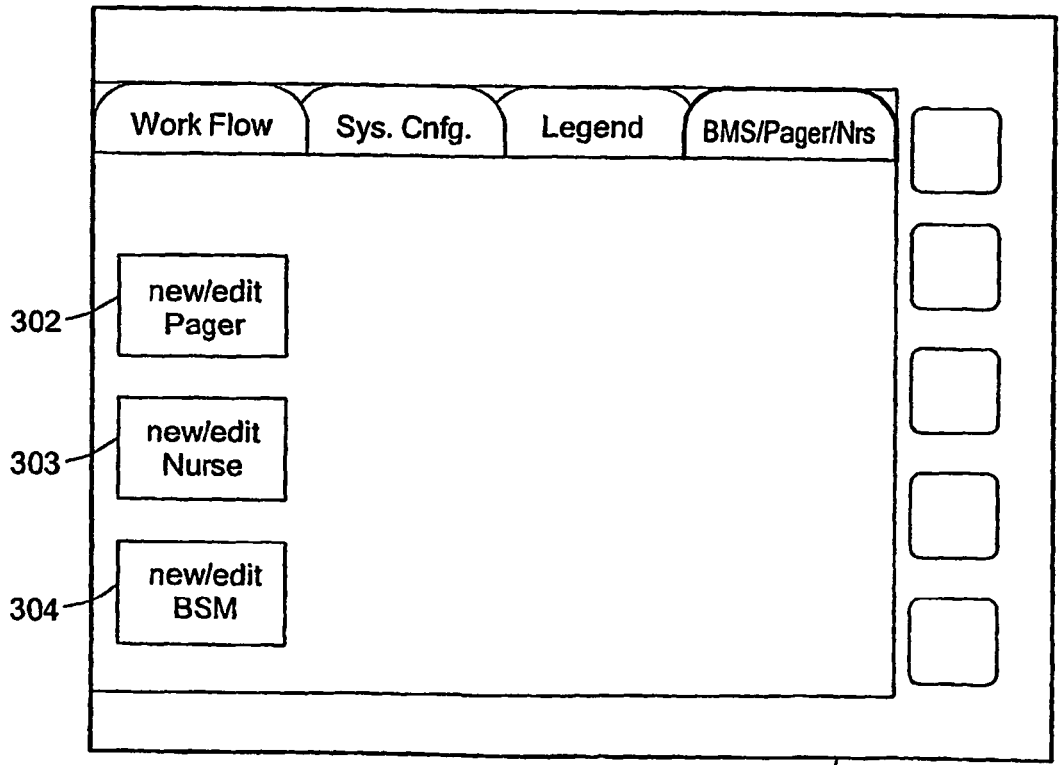
FIG. 3 is a sample display screen generated by the GUI of FIG. 1 illustrating a setup screen for adding or editing information relating to one or more pagers, nurses, and/or remote monitors for the patient activity monitoring system.

FIG. 3 depicts a sample display screen 300 generated by the GUI of FIG. 1, illustrating a setup screen for adding or editing information relating to one or more pagers, nurses, and/or remote monitoring units. In the illustrated embodiment, the setup screen 300 includes a new/edit pager button 302, a new/edit nurse button 303, and a new/edit BSM button 304. Accordingly, a user of the PAM system (e.g., an administrator) may add or edit pager, nurse, and remote monitor information by pressing the buttons 302-304, COG respectively, as displayed on the touch screen.

Figure 4A:
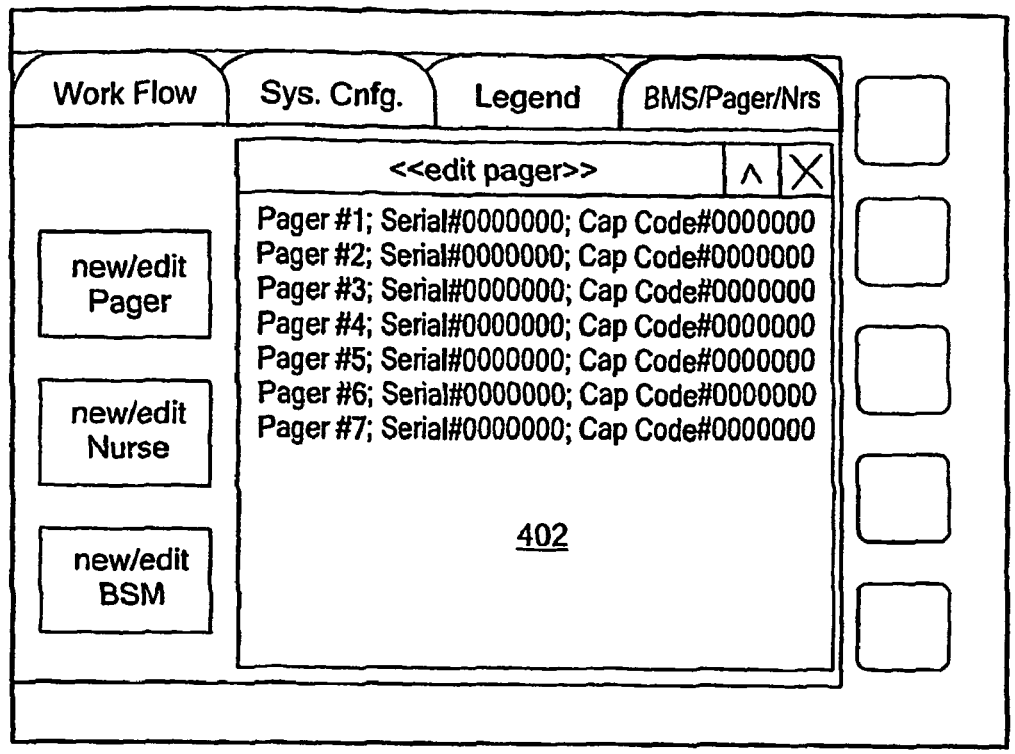
FIGS. 4a-4b are sample display screens generated by the GUI of FIG. 1 illustrating setup screens for adding/editing pager information.
Figure 4B:
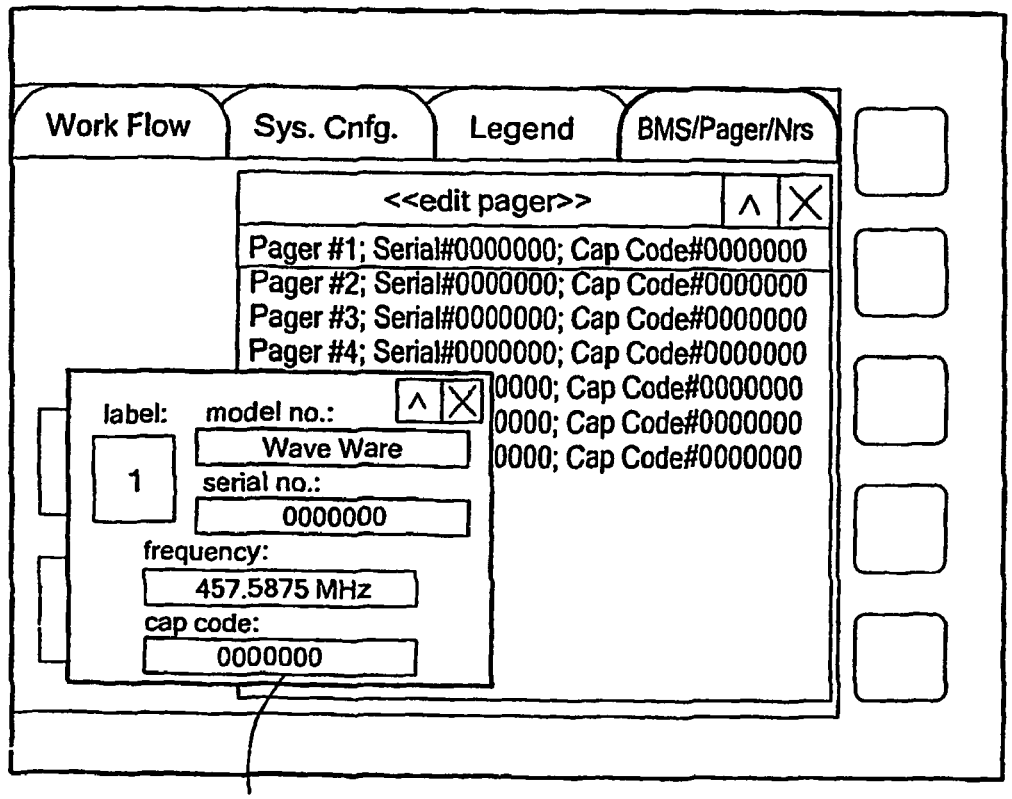

FIG. 4a depicts a pop-up window 402, which is displayed when the administrator presses the new/edit pager button 302 (see FIG. 3). In the illustrated embodiment, the pop-up window 402 includes information relating to pager numbers 1-7, such as the serial # and cap code # for each pager. The administrator may add or edit the pager information shown in the pop-up window by selecting one of the pagers 1-7 via a keyboard, mouse, or touch screen actuation. For example, in the event the administrator selects pager #1, a pop-up window 404 is displayed (see FIG. 4b) showing the model number, the serial number, the frequency, and the cap code number relating to pager #1. This pager #1 information may be changed by the administrator via the pop-up window 404 using the system keyboard. After the administrator finishes adding or editing the pager information, he or she may successively close the windows 404 and 402 by pressing the "X" button in the upper right-hand corner of the respective windows.

Figure 5A:
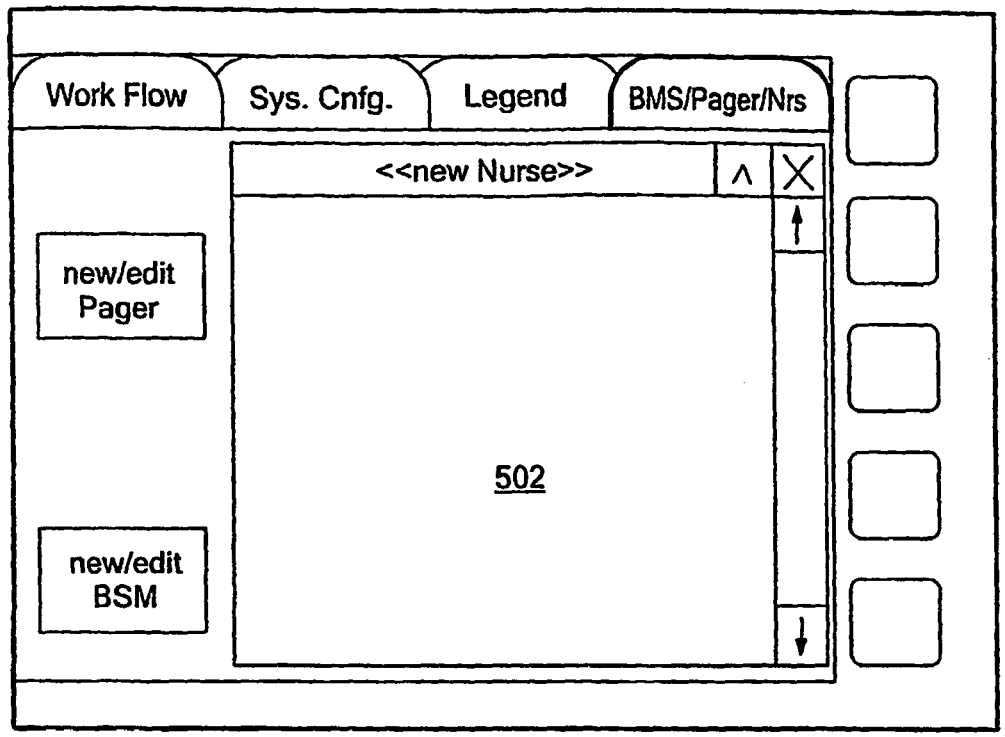
FIGS. 5a-5b are sample display screens generated by the GUI of FIG. 1 illustrating setup screens for adding/editing nursing staff information.
Figure 5B:
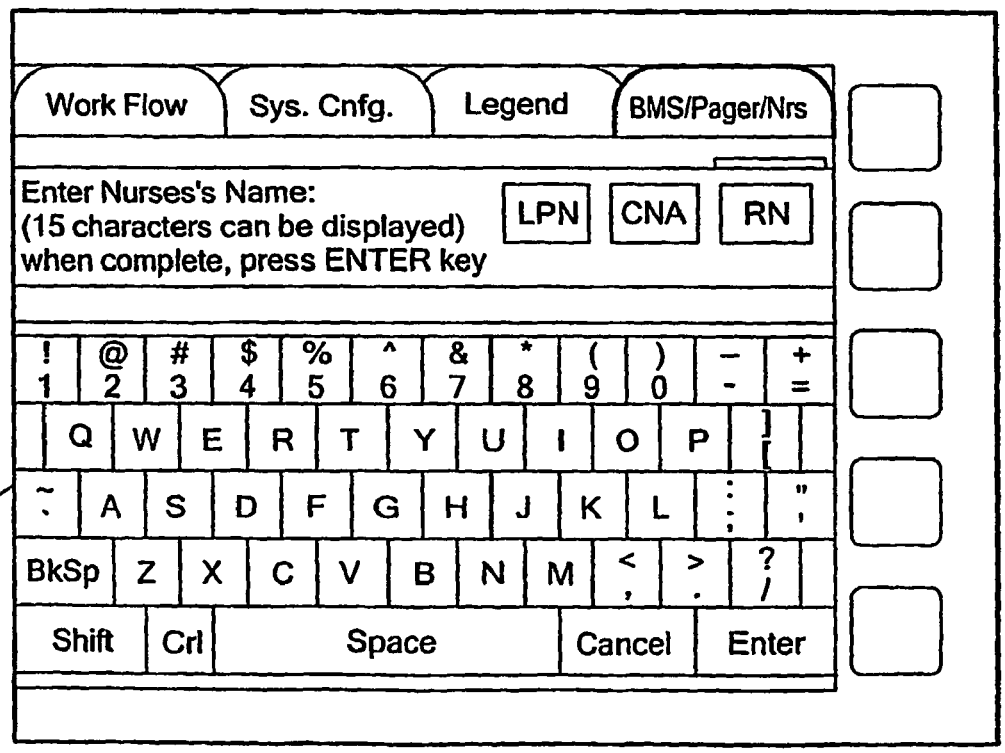

FIG. 5a depicts a pop-up window 502, which is displayed when the user presses the new/edit nurse button 303 (see FIG. 3). In the illustrated embodiment, the pop-up window 502 is used to add or edit information relating to the caregivers, e.g., the caregivers Jess K., CNA, Beth L., CNA, Ragina M., CNA, R-J Smith, CNA, Mary-Ann N., CNA, Jane D., CNA, Betty S., CNA, and S. Mary, CRN (see FIG. 8). In one embodiment, a virtual keyboard 504 (see FIG. 5b) may be displayed via a suitable keyboard or touch screen actuation and used to enter the desired caregiver information such as the caregiver name and shift assignment. After the administrator finishes adding or editing the caregiver information, he or she may close the window 502 by pressing the "X" button in the upper right-hand corner of the window.

Figure 6A:
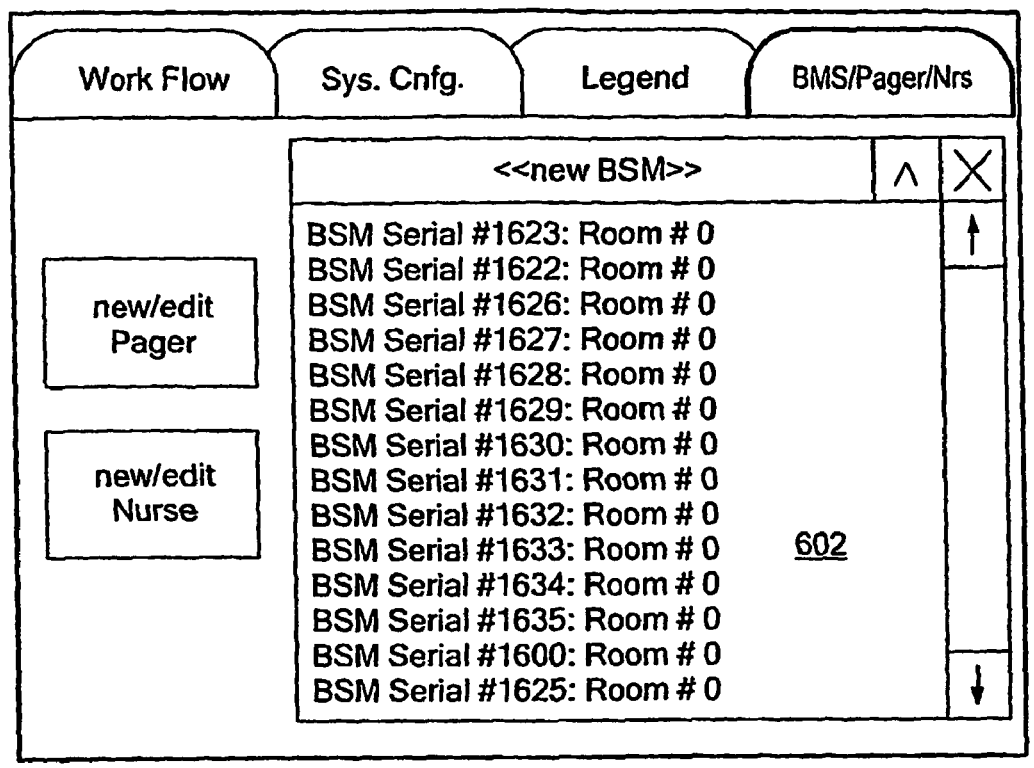
FIGS. 6a-6b are sample display screens generated by the GUI of FIG. 1 illustrating setup screens for adding/editing remote monitor information.
Figure 6B:
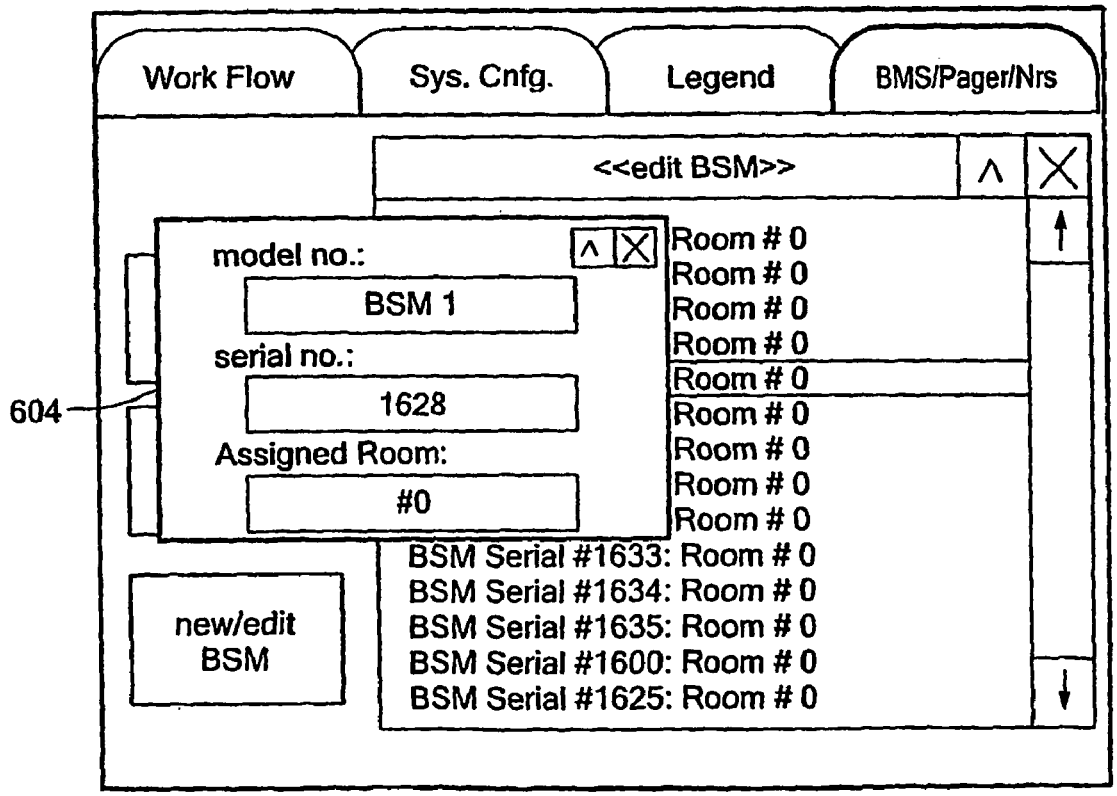

FIG. 6a depicts a pop-up window 602, which is displayed when the user presses the new/edit BSM button 304 (see FIG. 3). In the illustrated embodiment, the pop-up window 602 includes information relating to a plurality of remote monitoring units (BSMs), such as the serial # and room # for each pager. The administrator may add or edit the BSM information shown in the pop-up window by selecting one of the BSMs via a keyboard, mouse, or touch screen actuation. For example, in the event the administrator selects BSM Serial #1628, a pop-up window 604 is displayed (see FIG. 6b) showing the model number, the serial number, and the room associated with that BSM. This BSM information may be changed by the administrator via the pop-up window 604 using the system keyboard (or via a virtual keyboard). After the administrator finishes adding or editing the BSM information, he or she may successively close the windows 604 and 602 by pressing the "X" button in the upper right-hand corner of the respective windows.

Figures 7A, 7B:
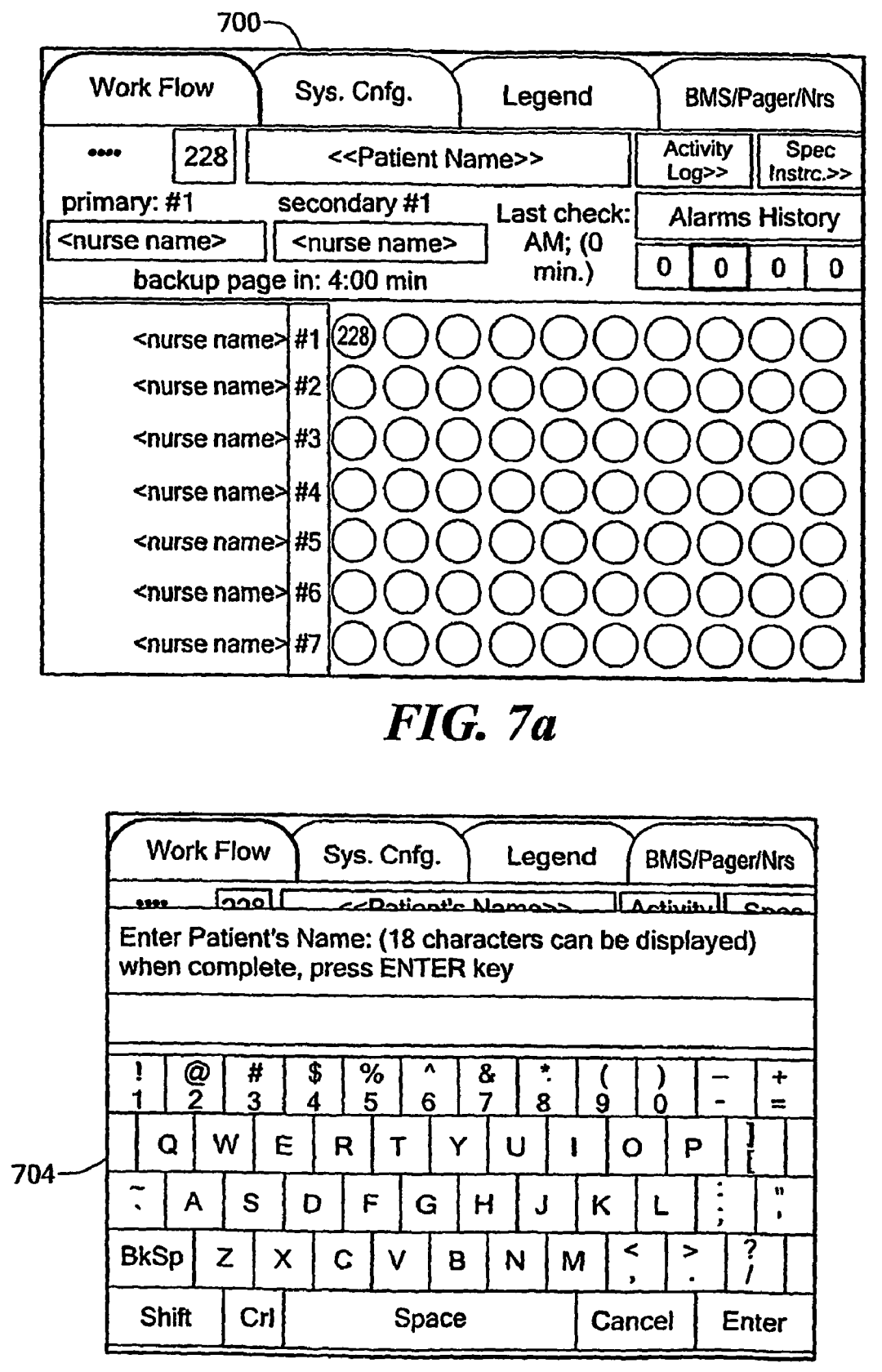

In the presently disclosed embodiment, the above-described pager, caregiver, and patient name associations are made using the Work Flow screen, which the administrator may access via the GUI by pressing the Work Flow tab displayed on the touch screen. FIG. 7a depicts a Work Flow screen 700 including the patient room number (e.g., "228"), display areas for the "Patient Name" and the "primary" and "secondary" caregiver names, indications of when the patient was lasted checked by a caregiver ("Last check: AM; (0 min.)") and when the displayed page is to be backed-up by the PAM system ("back up page in: 4:00 min."), respective buttons for accessing the patient's "Activity Log" and "Special Instructions" for the patient, and information relating to the patient's "Alarm History".

For example, to enter the patient's name, the administrator may press the Patient Name display area on the Work Flow screen 700 to cause a virtual keyboard 704 (see FIG. 7b) to be displayed, which may be employed to enter the desired patient information. The administrator completes the entry of the patient information by pressing the ENTER key on the virtual keyboard, thereby causing the virtual keyboard to be removed from the screen. Moreover, to enter information in the patient's activity log, the administrator may press the Activity Log display area on the Work Flow screen 700 to cause a Patient Activity Log panel 706 (see FIG. 7c) to be displayed, which may be employed to access or enter the desired patient activity information. The administrator completes the entry of the patient activity information by pressing the Activity Log display area again, thereby causing the panel 706 to be removed from the screen.

As described above, FIG. 8 depicts the main screen 800 indicating specific associations of caregivers, patient room numbers, and pagers in display areas 802, 804, and 806, respectively. It is noted that the main screen 800 may be advantageously employed to determine the current workload for each caregiver, and to balance the workload of the caregivers if warranted. For example, Ragina M., CNA, may have 10 patient room numbers associated with her pager. Further, six of her patients may be mobile (as indicated by the circular patient room icons, "●"), and five of her patients may require immediate attention (as indicated by the RED patient room icons). In this case, the administrator may conclude that Ragina M., CNA, has a heavy workload and that a degree of workload balancing is needed. In the presently disclosed embodiment, the administrator may dynamically balance the caregiver workload by pressing a patient room icon, e.g., the patient room icon 221, and then pressing a blank space such as the blank space to the right of patient room icon 236 (see FIG. 8), thereby reassigning patient room 221 from pager #3 to pager #4 (which is currently being used by R-J Smith, CNA). It is understood that additional patient room reassignments may be made in a similar manner.

FIG. 9a depicts a pop-up window 902, which is displayed when the user selects the pager #1 via a keyboard, mouse, or touch screen actuation. In the illustrated embodiment, the pop-up window 902 includes information relating to pager #1 such as the model name, the serial no., the frequency, the cap code, and the caregivers to whom the pager is assigned during each of the shifts 1-3. It is noted that the window 902 is employed by the users of the PAM system for informational purposes only—information cannot be added or edited via the window 902. It is further appreciated that corresponding information for the remaining pagers may be accessed by similarly selecting the desired pager number on the main screen 800 (see FIG. 8). After the administrator finishes accessing the information relating to pager #1, he or she may close the window 902 by pressing the "X" button in the upper right-hand corner of the window.

FIG. 9b depicts an activity log panel 906 corresponding to the pager #5, which is displayed when the user selects the pager #5 via a keyboard, mouse, or touch screen actuation. In the illustrated embodiment, the activity log panel 906 includes information such as the patient's room number (e.g., 263), a status code (e.g., WC), a color notation indicating either the status of the corresponding remote monitoring subsystem (e.g., "BLUE"—enabled or "BLACK"—disabled) or a level of assistance required by the patient (e.g., "GREEN", "YELLOW", or "RED"), a comment relating to the system or patient status (e.g., System Ready), and the time of the status check (e.g., 12:47:49 AM). An expanded view of the activity log panel 906 may be obtained by pressing the activity log display area 214 (see FIG. 2), and the activity log information may be scrolled by pressing the "↑" and "↓" arrows adjacent the displayed information. The content of the activity log panel 906 preferably comprises a simplified presentation of pertinent information needed by the caregiver. Further, both recent and historical patient information may be access from the data tables by the caregiver via the activity log panel 906.

It is noted that at the basic implementation level of the PAM system, the name of the caregiver need not be recorded in the Work Flow display. In the preferred embodiment, the default assumption is that pagers are essentially permanently associated with a specific remote monitoring unit. In this case, caregivers are made responsible for their assigned pager by an administrator outside of the PAM system. When a new caregiver comes on shift, he or she is expected to receive the pager assigned to them. This simplifies the administration of the PAM system because any changes in caregiver staff do not require caregiver or administration interaction with the system.

As described above, the PAM system 100 (see FIG. 1) is operative to convert patient information into one or more indications of the patients' status, and to convert information relating to respective remote monitoring subsystems into one or more indications of the subsystems' status. In the preferred embodiment, the PAM system recognizes the following patient activity/system states: 0-system power up, 1-patient nominal, 2-weight overload, 3-random movement, 4-swaying movement, 5-low activity, 6-edge limit, 7-rocking movement, 8-low battery, 9-cheek walk, 10-out of bed, 11-edge limit, 12-system malfunction, 13-system off, 14-LAN/pager malfunction, 15-nurse call, 16-incontinence, 17-seizure profile 1, 18-seizure profile 2, 19-alarm reset, and 20-patient presence detected. These patient activity/system states involve the interpretation of the condition of both equipment status inputs as well as patient status inputs from the smart sheet sensor and/or any other suitable sources. For example, each remote monitoring subsystem may include a memory (e.g., RAM and/or ROM) with preloaded objects representing the various patient actions listed above. Such objects may be formed by recording the output of the sensor in response to simulated movements by PAM system set-up personnel. The remote monitoring subsystem then does a comparison analysis of real sensed patient actions against the stored objects to find a fit, a best fit, a correlation, or any other suitable match. The severity of the activity is also detected by amplitude and/or type and used for displaying the appropriate colored/blinking icon alarm and alphanumeric message, and/or for sounding the appropriate audible alarm, at the central monitoring unit 102 and the corresponding caregiver pager(s) 106. It is contemplated that one or more algorithms such as an artificial intelligence algorithm employing a neural network and/or fuzzy logic or any other suitable algorithm may be used to recognize more complex patterns of behavior, e.g., specific types of seizures.

The embodiments disclosed herein will be better understood with reference to the following illustrative example. In this example, the remote monitoring unit for patient room number 263 is a bedside monitor and therefore the corresponding patient room icon displayed on the main screen by the GUI is rectangular ("■"). Further, the patient status alarms for patent room number 263 are customized as follows: patient room icon-GREEN, Patient Nominal; patient room icon-YELLOW, Random Movement; patient room icon-RED, Incontinence; and, patient room icon-RED (URGENT-blinking), audible alarm-ON, Out of Bed. It is understood that the appropriate patient room icons corresponding to the appropriate patient activity are displayed on the main display screen of the central monitoring unit. Moreover, the appropriate alphanumeric messages are displayed on the alphanumeric pager associated with room number 263 (e.g., pager #5). The audible alarm may sound, when necessary, at the central monitoring unit and/or the caregiver pager.

Figure 10:
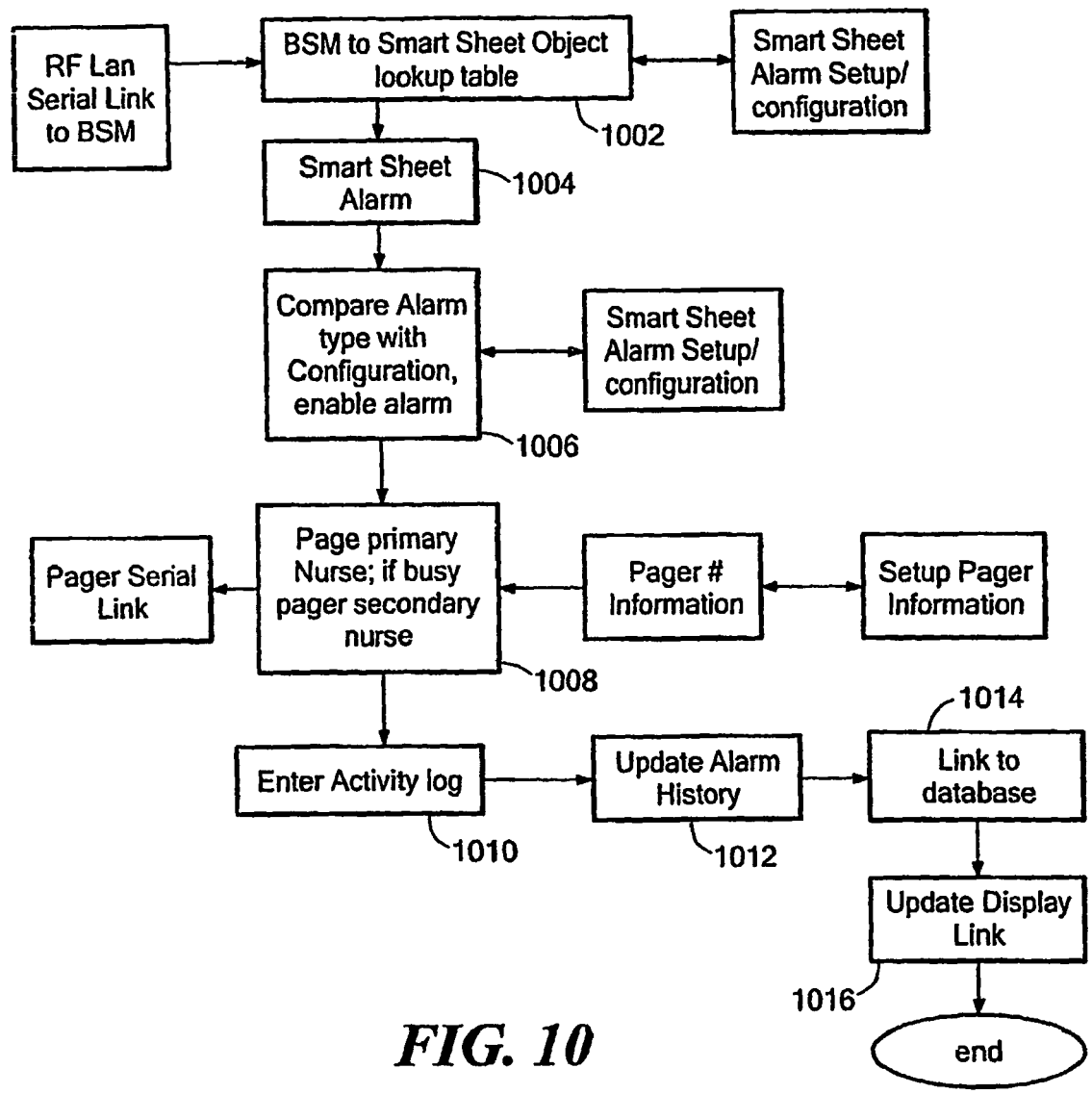
FIG. 10 is a flow diagram of an illustrative method of operating the patient activity monitoring system of FIG. 1.

A method of operating the presently disclosed Patient Activity Monitoring (PAM) system is illustrated by reference to FIG. 10. As depicted in step 1002, a Bedside Monitor (BSM) to smart sheet object lookup table receives RF LAN serial link to BSM data and accesses smart sheet alarm setup/configuration data. Next, a smart sheet alarm condition occurs, as depicted in step 1004. The alarm type is then compared, as depicted in step 1006, with the smart sheet alarm setup/configuration data, and in the event of a match, the appropriate alarm is enabled. Next, a primary nurse is paged, as depicted in step 1008, and in the event the primary nurse is busy, a secondary nurse is paged. It is noted that the PAM system pages the primary and/or secondary nurses using the appropriate setup pager information, the pager # information, and pager serial link information. The patient activity data is then entered, as depicted in step 1010, in the appropriate patient activity log. Next, the alarm history of the patient is updated, as depicted in step 1012. A communications link is then established, as depicted in step 1014, to the database to update the data table relating to the patient. For example, the database may be accessed over the Internet 120 (see FIG. 1). Finally, the display link to the main display screen is updated, as depicted in step 1016, thereby updating the patient status information at the central monitoring unit.

It will be appreciated by those of ordinary skill in the art that further modifications to and variations of the above-described patient activity monitor may be made without departing from the inventive concepts disclosed herein. Accordingly, the invention should not be viewed as limited except as by the scope and spirit of the appended claims.

What is claimed is:

1. A patient activity monitoring system, comprising:
a plurality of remote monitoring subsystems, each remote monitoring subsystem including a remote monitoring unit and at least one sensor device coupled to the remote monitoring unit, each sensor device being associated with a respective patient;
a plurality of user notification devices; and
a central monitoring unit communicably coupled to the plurality of remote monitoring subsystems and the plurality of user notification devices, the central monitoring unit having a graphical user interface,
wherein each sensor device is configured to detect at least one predetermined patient activity parameter of the respective patient associated therewith, and to transmit sensor data representative of the detected patient activity parameter to the remote monitoring unit coupled thereto,
wherein each remote monitoring unit is configured to receive sensor data, to process the sensor data to generate patient activity information corresponding to the sensor data, and to transmit the patient activity information to the central monitoring unit, the patient activity information including at least one representation of at least one type of physical activity of the respective patient associated with the sensor device, and a representation of a level of assistance required by the respective patient based at least in part on the at least one type of physical activity of the respective patient, and
wherein one or more of the graphical user interface and the plurality of user notification devices is operative to provide at least one alarm indication based at least in part on one or more of the at least one type of physical activity of one or more of the respective patients, and the level of assistance required by one or more of the respective patients.

2. The system of claim 1 wherein the central monitoring unit is configured to store the patient information in at least one database.

3. The system of claim 2 wherein the central monitoring unit is further configured to access selected patient information from the database, and to generate at least one report based on the selected information.

4. The system of claim 3 wherein the central monitoring unit is communicably coupleable to a wide area network, the central monitoring unit being further configured to transmit the at least one generated report over the wide area network.

5. The system of claim 4 wherein the central monitoring unit is configured for periodically transmitting the at least one report over the wide area network.

6. The system of claim 4 wherein the central monitoring unit is configured for automatically transmitting the at least one report over the wide area network.

7. The system of claim 1 wherein the at least one patient activity parameter is selected from the group consisting of patient weight data, random movement data, swaying movement data, low activity data, rocking movement data, cheek walk data, patient presence data, patient incontinence data, and patient seizure data.

8. The system of claim 1 wherein the graphical user interface is configured to receive inputs from a System user for making multiple associations of patients, caregivers, and user notification devices.

9. The system of claim 8 wherein the graphical user interface includes a first display area configured to display caregiver information, a second display area configured to display patient information, and a third display area configured to display user notification device information.

10. The system of claim 9 wherein the first, second, and third display areas of the graphical user interface are configured to communicate the multiple associations of patients, caregivers, and user notification devices to the system user.

11. The system of claim 9 wherein the at least one alarm indication provided by the graphical user interface includes at least one icon having a predetermined color and a predetermined shape, the icon being associated with a respective patient.

12. The system of claim 11 wherein the predetermined color of the icon is indicative of the level of assistance required by the respective patient.

13. The system of claim 11 wherein the predetermined shape of the icon is indicative of the level of assistance required by the respective patient.

14. The system of claim 11 wherein the predetermined color of the icon is indicative at the type of assistance required by the respective patient.

15. The system of claim 11 wherein the predetermined shape of the icon is indicative of the type of assistance required by the respective patient.

16. The system of claim 11 wherein the graphical user interface includes a first display area configured to display information corresponding to the at least one patient activity parameter.

17. The system of claim 1 wherein the central monitoring unit is communicably coupled to the remote monitoring subsystems and the user notification devices via at least one wireless network.

18. The system of claim 1 wherein the central monitoring unit is communicably coupled to the remote monitoring subsystems and the user notification devices via at least one land-based network.

19. The system of claim 1 wherein each user notification device comprises an alphanumeric pager.

20. A method of operating a patient activity monitoring system, comprising the steps of:
detecting at least one predetermined patient activity parameter of at least one respective patient by at least one sensor device, each sensor device being associated with a respective patient;
transmitting sensor data representative of the detected patient activity parameter to at least one remote monitoring unit by the sensor device, the remote monitoring unit being coupled to the at least one sensor device;
receiving sensor data from the sensor device by the remote monitoring unit;
processing the sensor data to generate patient activity information corresponding to the sensor data;
transmitting the patient activity information to a central monitoring unit by the remote monitoring unit, the patient activity information including at least one representation of at least one type of physical activity of the respective patient associated with the sensor device, and a representation of a level of assistance required by the respective patient based at least in part on the at least one type of physical activity of the respective patient; and
providing at least one alarm indication based at least in part on one or more of the at one type of physical activity of one or more of the respective patients, and the level of assistance required by one or more of the respective patients by one or more of a graphical user interface of the central monitoring unit and a plurality of user notification devices, the plurality of user notification devices being coupled to the central monitoring unit.

21. The method of claim 20 further including the step of storing the patient activity information in at least one database by the central monitoring unit.

22. The method of claim 21 further including the step of accessing selected patient activity information from the database and generating at least one report based on the selected patient activity information by the central monitoring unit.

23. The method of claim 22 further including the step of transmitting the at least one generated report over a wide area network by the central monitoring unit.

24. The method of claim 20 wherein the at least one patient activity parameter is selected from the group consisting of patient weight datr, random movement data, swaying movement data, low activity data, rocking movement data, cheek walk data, patient presence data, patient incontinence data, and patient seizure data.

25. The method of claim 20 further including the step of receiving inputs from a system user for making multiple associations of patients, caregivers, and user notification devices by the graphical user interface.

26. The method of claim 25 further including the steps of displaying caregiver information by a first display area of the graphical user interface, displaying patient activity information by a second area of the graphical user interface, and displaying user notification device information by a third area of the graphical user interface.

27. The of claim 26 further including the step of communicating the multiple associations of patients, caregivers, and user notification devices to the system user by the first, second, and third display areas of the graphical user interface.

28. The method of claim 20 wherein the at least one alarm indication provided by the graphical user interface includes at least one icon having a predetermined color and a predetermined shape, the icon being associated with a respective patient.

29. The method of claim 28 wherein the predetermined color of the icon is indicative of the level of assistance required by the respective patient.

30. The method of claim 28 wherein the predetermined shape of the icon is indicative of the level of assistance required by the respective patient.

31. The method of claim 28 wherein the predetermined color of the icon is indicative of the type of physical activity of the respective patient.

32. The method of claim 28 wherein the predetermined shape of the icon is indicative of a type of assistance required by the respective patient.

* * * * *

UNITED STATES PATENT AND TRADEMARK OFFICE
CERTIFICATE OF CORRECTION

PATENT NO.          : 7,336,187 B2                                    Page 1 of 1
APPLICATION NO.     : 10/531486
DATED               : February 26, 2008
INVENTOR(S)         : James E. Hubbard, Jr. et al.

It is certified that error appears in the above-identified patent and that said Letters Patent is hereby corrected as shown below:

Title page, item (75) Inventors, "Micahel D. Healy" should read --Michael D. Healy--;

Column 3, line 17, "a" should read --alarms--;

Column 7, line 66, "Pager #⇋Remote monitor⇋Room #⇋Patient name." should read --Pager # ↔ Remote monitor ↔ Room # ↔ Patient name.--;

Column 8, line 35, "COG" should be deleted;

Column 13, claim 8, line 2 "System" should read --system--;

Column 13, claim 14, line 26, "at the" should read --of the--;

Column 14, claim 20, line 5, "at one" should read --at least one--;

Column 14, claim 24, line 26, "datr," should read --data,--; and

Column 14, claim 27, line 40, "The of" should read --The method of--.

Signed and Sealed this

Thirteenth Day of October, 2009

David J. Kappos
*Director of the United States Patent and Trademark Office*